United States Patent [19]

Campbell et al.

[11] Patent Number: 4,885,413
[45] Date of Patent: Dec. 5, 1989

[54] PROCESS AND COMPOSITION FOR STABILIZATION OF AR-BROMINATED STYRENIC MONMER AGAINST PREMATURE STABILIZATION

[75] Inventors: Stephen M. Campbell, New England, W. Va.; John C. Wozny, Coolville, Ohio

[73] Assignee: Borg-Warner Chemicals, Inc., Parkersburg, W. Va.

[21] Appl. No.: 338,422

[22] Filed: Apr. 14, 1989

Related U.S. Application Data

[63] Continuation of Ser. No. 52,525, May 20, 1987, abandoned.

[51] Int. Cl.$^4$ .................. C07C 17/42; C07C 25/02
[52] U.S. Cl. ............................ 570/104; 570/264
[58] Field of Search ........................... 570/104, 264

[56] References Cited

U.S. PATENT DOCUMENTS

| 2,965,685 | 12/1960 | Campbell | 260/666.5 |
| 3,247,242 | 4/1966 | McGarvey | 260/486 |
| 3,248,440 | 4/1966 | Albert | 260/666.5 |
| 3,274,077 | 9/1966 | Hoffonberg et al. | 203/8 |
| 3,287,430 | 11/1966 | Haines et al. | 260/666.5 |
| 3,341,487 | 9/1967 | Albert et al. | 200/29.7 |
| 4,276,189 | 6/1981 | Jackisch | 252/1 |

FOREIGN PATENT DOCUMENTS 163428  6/1976  Czechoslovakia .
1230979  5/1971  United Kingdom .

OTHER PUBLICATIONS

Product Data Specification Sheets 1866 and S-226 (Pennsalt Rubber Chemicals 1969, 1967).
Frank R. L. and Adams C. E., "The Relative Efficiency of Some Polymerization Inhibitors", *Journal of the American Chemical Society*, vol. 68, p. 908 (1946).
Cubbon R. C. P. and Smith J. D. B., "The Properties of Nuclear Brominated Styrenes I . . .", *Polymer* vol. 10, No. 7, p. 479–487 (1969).
Cubbon R. C. P. and Smith J. D. B. "The Properties of Nuclear Brominated Styrenes II–The Copolymerization of Dibromostyrene and 2, 4, 5–Tribromo styrene with Styrene," *Polymer* vol. 10 No. 7, p. 489–493 (1969).
Imoto M. et al., "Polar Effects in Radial Polymerization of p–Substituted Styrenes", *Die Makromolekulare Chemie*, vol. 86 p. 217–230 (1965).

Primary Examiner—J. E. Evans
Attorney, Agent, or Firm—Lowe, Price, LeBlanc, Becker & Shur

[57] ABSTRACT

A process and composition for stabilizing ar-brominated styrene polymer against polymerization which mixes an ar-brominated styrene monomer with a stabilizing amount of N,N-dialkylhydroxylamine to produce a stabilized monomer and novel stabilized compositions.

5 Claims, 1 Drawing Sheet

N,N-DIETHYLHYDROXYLAMINE STABILIZED DIBROMOSTYRENE @ 50 C

PROCESS AND COMPOSITION FOR STABILIZATION OF AR-BROMINATED STYRENIC MONMER AGAINST PREMATURE STABILIZATION

This application is a continuation, of application Ser. No. 07/052,525, filed May 20, 1987, now abandoned.

BACKGROUND OF THE INVENTION

The invention relates to polymerization retarders and inhibitors in general and to stabilizing agents for prevention of premature polymerization of ar-brominated styrene monomer in particular.

Vinyl aromatic compounds tend to polymerize on standing. During the manufacture, shipping, and storage of these compounds, inhibitors are normally added to prevent or highly retard polymerization until such time that these compounds are intentionally converted to polymers.

Dozens of stabilizing agents for prevention of undesirable polymerization of monomers in general have been reported in the literature. As noted by Czechoslovakian Patent Document No. 163,428 (Konecny et al) compositions which are known to stabilize one or more monomers include: sulfur, copper, silver, gold, activated carbon, triphenylarsine, $NH_3$, diazoaminobenzene, some diolefins, phenylacetylene, sym-trinitrobenzene, p-benzoquinone, acetaldehyde, aniline condensates, N,N'-dibutyl-o-phenylenediamine, N-butyl-p-aminophenol, 2,4,6-triphenylphenoxyl, pyrogallol, pyrocatechol, hydroquineone, alkyl-substituted pyroactechols, dialklhydroquinone, 2,4,6-di-chloronitrophenol, halogen-ortho-nitrophenols, alkoxyhydroquinone, mono-, di-, and polysulfides of phenols and pyrocatechols, aromatic nitrocompounds, amines, thiols, oximes or hydrazones of quinone, phenothiazine, dialkylhydroxylamines, and nitro compounds. However, as also noted by Konecny et al only a few of the known stabilizers are commercially employed with benzoquinone, hydroquinone, and tert-butylpyrocatechol mentioned by name. The other stabilizers have various shortcomings including undesirable levels of toxicity, explosiveness, or insufficient stabilizing activity. Also, many of the above listed compounds are noted to be stabilizers in conjunction with only a limited group of monomers. Konecny et al suggest use of a synergistic mixture of 2,4 dinitro-o-cresol and diethylhydroxylamine with styrene and divinyl benzene.

In 1960 a process for stabilizing vinyl aromatics such as styrene was described in U.S. Pat. No. 2,965,685 (Campbell) which utilized N,N-dialkylhydroxylamines such as N,N-diethylhydroxylamine (DEHA). Recommended levels of inhibitor are said to be from about 0.001% to about 5% by weight.

In 1966 aliphatic carboxylic acid salts of DEHA were described as stabilizers for aromatic vinyl compounds such as styrene in U.S. Pat. No. 3,248,440 (Albert).

While diethylhydroxylamine-containing compositions have been described as among a plethora of types of chemicals useful for stabilizing vinyl aromatic compounds such as styrene, its use with brominated styrenes has not been addressed. Only a few compositions have been described as useful for stabilizing ar-brominated styrenes such as dibromostyrene.

In British Patent Document No. 1,230,979, dibromostyrene (DBS) is described as being stabilized by picric acid or by a mixture of picric acid with a quinone or phenol such as hydroquinone, benzoquinone and t-butyl catechol. Unfortunately picric acid has the undesirable characteristics of coloring monomers bright yellow and, when concentrated, being shock sensitive.

Also, U.S. Pat. No. 4,276,189 (Jackisch) describes a process for retarding polmerization of dibromostyrene by addition of a metal oxide such as magnesium, calcium, or zinc oxide with or without an additional stabilizing agent such as 4-tert-butylcatechol and most benzoquinones.

SUMMARY OF THE INVENTION

According to the present invention, a novel process for stabilizing ar-brominated styrene monomer against polymerization is described in which ar-brominated styrene monomer such as mono-, di-, or tri-bromostyrene or mixtures thereof are contacted or admixed with a stabilizing or polymerization retarding amount of N,N dialkylhydroxylamine to produce stabilized monomer.

Surprisingly, amounts of N,N-diethylhydroxylamine (DEHA) as low as 500 ppm will stabilize ar-brominated styrene monomer for a period of 300 hours at temperatures at or below 50 degrees C.

The inventive process produces a stabilized ar-brominated styrene monomer composition which resists premature polymerization which may be sorted, handled, transported, and subsequently polymerized with a greater deal of control, safety and economy relative to unstabilized monomer. In particular, dibromostyrene monomer may be maintained for a longer period of time without undesirable polymerization.

DETAILED DESCRIPTION OF THE INVENTION

Figure 1:
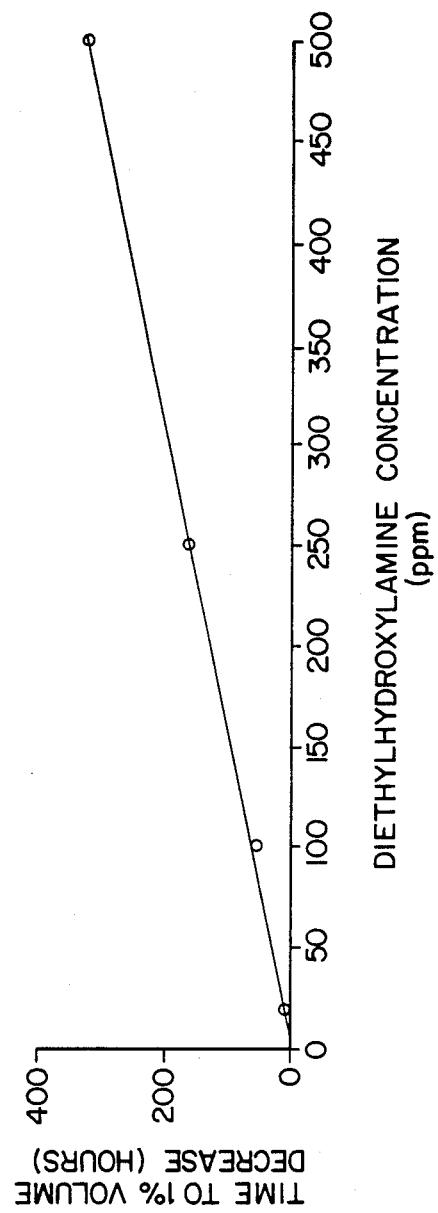
FIG. 1 is a graph comparing DEHA concentration against time required to show a one percent volume decrease.

The process of the present invention is useful to stabilize ar-brominated styrene monomer against premature polymerization. It is desirable to prevent or retard the rate of polymerization in order to ship or store monomer until required for use. Brominated styrenes such as dibromostyrene have been suggested as a flame retardant monomer for use in making flame retardant materials.

There are several reasons why, in spite of the large number of inhibitors that have been discovered for vinyl aromatic compounds including diethylhydroxylamine, so few would be expected to find applicability with dibromostyrene.

Brominated styrenes have shown a markedly greater tendency to polymerize than styrene monomer alone. Table I shows polymerization constants ($K_p$) and termination constants ($K_t$) for styrene and mono-substituted halostyrene monomers in dimethylacetamide at about 30 degrees C. as published by Imoto et al, *Makromol. Chem.*, (1965), 86, 217.

TABLE I

| Monomer | $K_p$ l/mole sec | $K_t \times 10^6$ l/mole sec |
|---|---|---|
| Styrene | 106 | 108 |
| Styrene p-F | 112 | 127 |
| Styrene p-Cl | 150 | 77 |
| Styrene p-Br | 186 | 46 |

As shown in Table I, the rates of polymerization ($K_p$) for styrene and substituted styrene monomers indicates that halogenated styrenes are significantly more reactive than unsubstituted styrene and therefore more difficult to stabilize against premature polymerization. Also, since the termination rate ($K_t$) for an active bromostyrene radical is lower than that for styrene or its p-F or p-Cl analogs, the brominated styrenes are especially difficult to stabilize. With a lower termination rate ($K_t$) a greater amount of polymer is formed for each active free radical than for monomers having high $K_t$ values. Cubbon and Smith in their article entitled, "The Properties of Nuclear Brominated Styrenes I—The Synthesis and Polymerization of Dibromostyrene and Tribromostyrene," Polymer, Vol. 10, no. 7 (1969) pp 479–487, (which article is hereby incorporated by reference) have shown in their FIG. 1 the polymerization rate of dibromostyrene to be more than 10 times as active as styrene.

It is also noted that dibromostyrene formed by conventional processes may be a mixture of mono-, di-, and tri-bromostyrenes. Tribromostyrene has an even greater tendency to polymerize than the highly reactive dibromostyrenes. Cubbon and Smith, supra, further state the order of rates of thermal polymerization to be: 2,4,5-tribromostyrene>2,4- and 3,4 dibromostyrene >> styrene.

Many known stabilizers for styrene are ineffective or poor polymerization inhibitors for substituted styrenes. Also, many free radical stabilizers are effective at high temperatures, but do not follow a first order stability relationship to room temperature. Therefore, the stabilizing capacity of inhibitors should be determined at or near the actual conditions contemplated.

Following are examples given to illustrate the process and compositions of the invention. Evidence of polymerization was followed by the dilitometric method. All examples were conducted at 50° C. and at atmospheric pressure. The experimental methodology was as follows:

Monomer samples were prepared for testing by introducing a precisely known weight of a test inhibitor into a clean 9 inch Kimble 2075C cream test bottle. (A cream test bottle consists of a large flat bottomed bulb which tapers into a long narrow neck. The neck is calibrated in arbitrary units from 0 to 50.) A known weight of monomer was then added in portions with intermittent mixing to yield the indicated concentration of the test substance in the monomer. Each bottle was stoppered and mixing was completed by inverting the bottle 25 times. (The volumes were precalculated to yield a level of about 25 on the scale.) The stopper was removed and the bottle was loosely covered with aluminum foil to eliminate evaporation. The above procedure and use of a long narrow necked bottle acts to minimize air exposure. Minimum air exposure is desirable as an experimental condition because it simulates reasonable expected static storage conditions for bulk handling of this monomer. The bottles were immersed into a constant temperature bath at 50.00°±0.02° C. and allowed to equilibrate. After equilibration, the volume was readjusted to exactly 25.0 on the bottle scale. The volume change was recorded versus time to monitor any conversion to polymer. A 5 unit change on the bottle scale was determined to be equal to a 1% change in total volume at midscale.

The styrene used in the examples was commercially available and used as received from Cosden Chemical Company. The dibromostyrene was obtained as an experimental monomer mixture of monobromostyrene, dibromostyrene, and tribromostyrene from Great Lakes Chemicals under the name of "Dibromostyrene" and from Ethyl Corporation under the name of Satex RB-25. No difference between the two monomers was observed with respect to stabilizer response. N,N-diethylhydroxylamine was purchased from Aldrich Chemical Company at 97% purity under the product designation of D 9720-7.

The results are shown in Table 2 for ease of comparison. Examples 1–3 and 8 are comparative examples and examples 4–7 and 9 are of the present invention.

TABLE 2

| Example | Inhibitor | Hours to % Volume Decrease @ 50° C. | | |
|---|---|---|---|---|
| | | 0.2% | 0.5% | 1.0% |
| 1. Commercial STYRENE | 10 ppm t-BC | 50 | 131 | 310 |
| 2. DIBROMO-STYRENE | No Stabilizer | 1.5 | 3 | 7 |
| 3. DIBROMO-STYRENE | 250 ppm t-BC | 10 | 21 | 27 |
| 4. DIBROMO-STYRENE | 20 ppm DEHA | | | 15 |
| 5. DIBROMO-STYRENE | 100 ppm DEHA | 19 | 28 | 52 |
| 6. DIBROMO-STYRENE | 250 ppm DEHA | 40 | 99 | 180 |
| 7. DIBROMO-STYRENE | 500 ppm DEHA | 60 | 145 | 320 |
| 8. DIBROMO-STYRENE* | 250 ppm t-BC | | | 0.4 |
| 9. DIBROMO-STYRENE* | 500 ppm DEHA + 250 ppm t-BC | | | 1.5 |

*Polymerization intentionally begun with initiator

EXAMPLE 2 (CONTROL—NOT OF THE INVENTION)

As shown by the data in example 2 of Table 2, dibromostyrene monomer, without any stabilizing agent, quickly polymerizes until a one percent drop in volume occurs after only seven hours. Thus, without inhibitor the original monomer quickly converts to polymer necessitating costly removal steps and rendering that portion of the monomer unsuitable for its intended purpose. The stability against premature polymerization of unstabilized dibromostyrene (DBS) may vary from one to several hours at 50° C. when tested with minimum exposure to oxygen from the air.

EXAMPLES 1 AND 3 (NOT OF THE INVENTION)

Examples 1, and 3 in Table 2 show that dibromostyrene stabilized with 250 ppm t-butyl catechol (t-BC) is less than one tenth as stable as the commercial styrene sample containing only 10 ppm t-butyl catechol as measured by a 1% volume decrease. While t-BC added to dibromostyrene will provide some degree of stabilization, it is not comparable to the level of stabilization of styrene with t-BC.

EXAMPLES 4-7

Examples 4, 5, 6, and 7 in Table 2 show that the induction periods before undesirable polymerization (1% volume decrease) for 500 ppm, 250 ppm, 100 ppm, and 20 ppm N,N-diethylhydroxylamine in dibromostyrene were 320, 180, 52 and 15 hours respectively. FIG. 1 demonstrates that the relationship between stability and concentration was essentially linear. A stabilizing amount is defined as sufficient added inhibitor to stop or retard polymerization for a time exceeding that observed for a monomer without added inhibitor.

Comparison of Examples 3 and 6 in Table 2 shows that DEHA is a superior stabilizer for dibromystyrene relative to ti-butylcatechol. At equal concentrations by weight the DEHA was four to six times as effective as t-butylcatechol. When calculated on a molar basis the DEHA is as much as 12 times as efficient at minimizing polymer formation as t-butylcatechol.

EXAMPLES 8-9

Examples 8 and 9 demonstrate the ability to initiate polymerization when desired by addition of a polymerization initiator. DBS containing 500 ppm, N,N-diethylhydroxylamine and 250 ppm t-BC began rapidly polymerizing in 1.5 hours when initiated in bulk with a low radical flux polyerization initiator such as 0.1% by weight of a commercially available initiator sold under the trade name VAZO 52 by E.I. DuPont de Nemours Co. at 50° C. DBS containing only the t-BC exhibited rapid polymerization onset after 0.4 hours under the same conditions. In both cases polymerization continued to form a glassy solid homopolymer.

The high reactivity of dibromostyrene toward polymerization tends to limit the storage stability and handling latitude of this monomer. Surprisingly, stabilization of the dibromostyrene with a dialkylhydroxylamine such as diethylhydroxylamine shows that dibromostyrene may be stabilized to a level comparable to commercial styrene. Also, N,N-diethylhydroxylamine inhibitor has the added advantage that it can be readily overcome by free radical initiators when used at levels which provide adequate storage stability in dibromostyrene. An upper allowable N,N-diethylhydroxylamine concentration appears to be limited only by any retarding effect on polymerizability during reaction conditions. Sufficient storage stability is achieved in DBS at N,N-diethylhydroxylamine concentrations well below the level where polymerizability is adversely affected.

Other dialkylhydroxylamines are believed to be suitable, especially linear, branched-chair or cyclic diloweralkylhydroxylamines having one to seven carbon atoms.

The above examples serve only to illustrate the invention and its advantages and should not be interpreted as limiting since further modifications of the disclosed invention will be apparent to those skilled in the art. All such modifications are deemed to be within the scope of the invention as defined by the following claims.

What is claimed is:

1. A process for retarding rapid polymerization of ar-brominated styrene monomer and maintaining the ar-brominated styrene monomer at a level of 99% of its original volume for a period of 300 hours at temperatures at or below 50° C., said process comprising admixing a polymerization retarding amount of N,N-dialkylhydroxylamine with ar-brominated styrene monomer, said retarding amount being sufficient to produce a stable monomer which maintains 99% of its original volume for a period of 300 hours at temperatures at or below 50° C.

2. A process as defined in claim 1 wherein said ar-brominated styrene comprises dibromostyrene monomer.

3. A process as defined in claim 1, wherein ar-brominated styrene monomer comprises a mixture of ar-brominated styrenes forming a composition having from about 0.8 to about 3.2 bromines per aromatic ring.

4. A process as defined in claim 1 wherein said N,N-dialkylhydroxylamine comprises N,N-diethylhydroxylamine.

5. Ar-brominated styrene monomer stabilized against rapid polymerization, comprising a polymerization retarding amount of N,N-dialkylhydroxylamine, said retarding amount being sufficient to produce a stable monomer which maintains 99% of its original volume for a period of 300 hours at temperatures at or below 50° C.

* * * * *